United States Patent
Johs et al.

[19]

[11] Patent Number: 5,963,325
[45] Date of Patent: *Oct. 5, 1999

[54] DUAL VERTICALLY ORIENTED TRIANGULAR SHAPED OPTICAL RETARDER ELEMENT FOR USE IN SPECTROSCOPIC ELLIPSOMETER AND POLARIMETER SYSTEMS

[75] Inventors: Blaine D. Johs; Craig M. Herzinger; Steven E. Green, all of Lincoln, Nebr.

[73] Assignee: J.A. Woollam Co. Inc., Lincoln, Nebr.

[ * ] Notice: This patent is subject to a terminal disclaimer.

[21] Appl. No.: 09/225,076

[22] Filed: Jan. 4, 1999

Related U.S. Application Data

[63] Continuation of application No. 08/997,311, Dec. 23, 1997.

[51] Int. Cl.$^6$ ............................................. G01J 4/00
[52] U.S. Cl. ................................. 356/364; 356/369
[58] Field of Search .................... 356/364–369; 250/225; 359/352, 486, 487

[56] References Cited

U.S. PATENT DOCUMENTS

| | | | |
|---|---|---|---|
| 548,495 | 10/1895 | Abbe | 359/833 |
| 2,447,828 | 8/1948 | West | 359/833 |
| 2,815,452 | 12/1957 | Mertz . | |
| 3,428,388 | 2/1969 | Kuebler et al. . | |
| 3,439,968 | 4/1969 | Hansen et al. . | |
| 3,817,624 | 6/1974 | Martin | 356/138 |
| 4,053,232 | 10/1977 | Dill et al. | 356/369 |
| 4,221,464 | 9/1980 | Pedinoff et al. | 350/152 |
| 4,556,292 | 12/1985 | Mathyssek et al. | 350/394 |
| 4,733,926 | 3/1988 | Title | 350/1.1 |
| 4,961,634 | 10/1990 | Chipman et al. | 350/403 |
| 5,016,980 | 5/1991 | Waldron | 350/286 |
| 5,177,635 | 1/1993 | Keilmann | 359/352 |
| 5,187,611 | 2/1993 | White et al. | 359/599 |
| 5,402,260 | 3/1995 | Tsuneda et al. | 359/282 |
| 5,475,525 | 12/1995 | Tournois et al. | 359/245 |
| 5,548,427 | 8/1996 | May | 359/73 |

*Primary Examiner*—Hoa Q. Pham
*Attorney, Agent, or Firm*—James D. Welch

[57] ABSTRACT

A retarder system suitable for use in ellipsometers and polarimeters is configured from a first triangular shaped element with reflective outer surfaces, and a second triangular shaped element with reflective inner surfaces. In addition, a non-Brewster angle polarizer system suitable for use in ellipsometers and polarimeters is configured from two plates which are oriented other than parallel with respect to one another. A beam of electromagnetic radiation entered to the retarder system or polarizer system exits with a changed state of polarization, but with essentially no deviation or displacement in the direction of propagation, even when, in the case of the retarder system, it is caused to rotate about the locus of the beam of electromagnetic radiation.

9 Claims, 7 Drawing Sheets

$$\frac{d}{h} = 2 \cdot \tan(\phi), \text{ where } \phi = \alpha + \sin^{-1}\left(\frac{\sin(90-\alpha)}{n}\right)$$

$$d = 2h\left(\frac{1}{\tan(\alpha)} + \tan(\phi)\right), \text{where } \phi = \alpha + \sin^{-1}\left(\frac{\sin(90-\alpha)}{n}\right)$$

DUAL VERTICALLY ORIENTED TRIANGULAR SHAPED OPTICAL RETARDER ELEMENT FOR USE IN SPECTROSCOPIC ELLIPSOMETER AND POLARIMETER SYSTEMS

This application is a continuation of Ser. No. 08/997,311 filed Dec. 12, 1997.

TECHNICAL FIELD

The present invention relates to ellipsometer/polarimeter systems, and more particularly to polarizer systems with high extinction ratios which can be used at infrared wavelengths, and to retarder systems with retardation vs. wavelength dispersion characteristics within a range of acceptability. In addition, present invention optical elements do not introduce significant deviation and/or displacement into the propagation direction of a beam of electromagnetic radiation caused to interact therewith, even when, for instance, a present invention retarder system is caused to continuously rotate, and certain present invention optical elements demonstrate limited immunity to beam alignment changes.

BACKGROUND

Polarimeters and ellipsometers are comprised of optical elements such as polarizer and retarder systems. Polarimeter systems allow the polarization state of a polarized beam of electromagnetic radiation to be determined, and ellipsometer systems allow detection of change in polarization state of a polarized beam of electromagnetic radiation resulting from interaction with a sample system to be determined, said change in polarization state being associated with optical and physical properties of said sample system. For general information it is noted that the polarization state of a polarized beam of electromagnetic radiation is determined by:

a. ratio of orthogonal components, (related to PSI);

b. phase angle between said orthogonal components, (related to DELTA);

c. absolute value of one orthogonal component; and d. the direction of rotation, or handedness.

Continuing, in the Ultraviolet-Visible-Near Infrared spectral region, (ie. wavelengths between one-hundred-ninety (190) and two-thousand (2000) nanometers (nm)) polarizer elements which exhibit nearly ideal characteristics are readily available. However, no polarizer systems are available which provide ideal characteristics in the infrared range of wavelengths, (ie. wavelengths in the range of approximately two (2) to fifty (50) microns). There is thus identified a need.

As well very few retarders are available which provide even a remotely achromatic response over any wavelength range of from in the infrared to say, eight hundred (800) nm and above. Again, a need is thus identified.

An ideal polarizer would pass only linearly polarized electromagnetic radiation aligned with the fast axis thereof, and would reject all electromagnetic radiation in an orthogonal orientation. That is, the extinction ratio would be essentially infinite. The Mueller Matrix for an ideal polarizer is provided below:

$$\text{POLARIZER IDEAL} = \begin{bmatrix} 1 & 1 & 0 & 0 \\ 1 & 1 & 0 & 0 \\ 0 & 0 & 0 & 0 \\ 0 & 0 & 0 & 0 \end{bmatrix}$$

An ideal Retarder system should enter a phase retardation between orthogonal components of polarized electromagnetic radiation without preferentially modifying the intensity of either orthogonal component thereof. The Mueller Matrix of an ideal Retarder is:

$$\text{RETARDER IDEAL} = \begin{bmatrix} 1 & 0 & 0 & 0 \\ 0 & 1 & 0 & 0 \\ 0 & 0 & \cos(r) & \sin(r) \\ 0 & 0 & -\sin(r) & \cos(r) \end{bmatrix}$$

where "r" is the entered retardence.

As even very good Retarder systems tend to preferentially modify one orthogonal component of an electromagnetic beam of radiation, (including those presented in this Disclosure), it is necessary to modify said Mueller Matrix to account for said effect. The Mueller Matrix of a Retarder system which accounts for preferential modification of one orthogonal component of a polarized beam of electromagnetic radiation is:

$$\text{RETARDER LESS IDEAL} = \begin{bmatrix} 1 & -\cos(2\psi) & 0 & 0 \\ -\cos(2\psi) & 1 & 0 & 0 \\ 0 & 0 & \sin(2\psi)\cos(r) & \sin(2\psi)\sin(r) \\ 0 & 0 & -\sin(2\psi)\sin(r) & \sin(2\psi)\cos(r) \end{bmatrix}$$

where "r" is again the retardence entered. Note that where Retarder system PSI ($\psi$) is forty-five (45) degrees, said Mueller Matrix reduces to the ideal Mueller Matrix.

It is additionally noted that the value of "r" should be in a range where an ellipsometer system in which it is a component is not severely sensitive to changes therein as, for instance, a function of wavelength. In Rotating Compensator Ellipsometers, it is disclosed that a value of "r" between ninety (90) and one-hundred-fifty (150) degrees is generally acceptable. It is also noted that typical off-the-shelf Retarder systems often exhibit an "r" with a (1/wavelength) response such that "r" values are not within said 90 to 150 degree range, when observed over a wavelength range of say, two-hundred-fifty (250) to one-thousand (1000) nm.

It is a requirement of an ideal optical element that a beam of electromagnetic radiation caused to interact therewith not have its direction of propagation deviated or displaced thereby. This is especially critical where an optical element must be rotated in use.

It is further desirable that an optical element not exhibit sensitivity of, for instance, extinction ratio, or retardence entered between orthogonal components of an electromagnetic beam of radiation caused to interact therewith, as a function of beam alignment with respect thereto.

As well, it is desirable that optical elements be easy to fabricate and that fabrication be from easily obtainable materials.

The practice of ellipsometry requires that data reflecting change in polarization state of an electromagnetic beam of radiation resulting from interaction with a sample system be obtained and that said data be compared to data generated by use of a proposed mathematical model. Said mathematical model must take into account all nonidealities of optical elements present in the ellipsometer utilized. It is thus preferable to have as few nonidealities present in optical elements as is possible, in order to simplify mathematical model complexity.

With an eye to the present invention, a Search of Patents was conducted. Said Search was focused on polarizers suitable for use in the infrared, and on compensators which might provide relatively stable retardation over a range of wavelengths without imposing deviation or displacement in a beam of electromagnetic radiation caused to pass therethrough.

Regarding compensators Patents were found which show elements with geometry somehow similar to geometry of present invention compensators, but the present invention use was not found. In particular attention is directed to the Figure in Pat. No. 548,495 to Abbe; FIG. 2 in Pat. No. 4,556,292 to Mathyssek et al.; FIGS. 1 & 4 in Pat. No. 5,475,525 Tournois et al.; and FIG. 10 in Pat. No. 5,016,980 Waldron. Pat. No. 3,817,624 to Martin and Pat. No. 2,447,828 to West were also identified.

Regarding polarizers, Patents were also identified. For Instance, Pat. No. 4,221,464 to Pedinoff et al. shows a Double Plate Brewster Angle Polarizer (10) (12) which serves to avoid back reflections, which is combined with a Wire Grid Polarizer (28) present on Plate (14). A purpose of the invention is to increase the extinction coefficient of the Wire Grid Polarizer, by combining it with the Double Plate Brewster Angle Polarizer (10) (12).

A Pat. No. 5,177,635 to Keilmann, shows an Infrared Polarizer Structure of patterned metal strips on a transparent material, but does not suggest a dual polarizer arrangement.

While a Pat. No. 4,961,634 to Chipman et al., shows two polarizers made of CdS and CdSe respectively, in series, there is no angled arrangement therebetween suggested.

A Pat. No. 452 to Mertz, shows multiple Wire Grids oriented at angles with respect to one another. The system is an Interferometer in which said one said Wire Grid is rotated with respect to another.

A Pat. No. 3,439,968 to Hansen, shows an Infrared Brewster Angle Polarizer.

A Pat. No. 3,428,388 to Kuebler et al., shows a UV "Biotite" based Brewster Angle Polarizer.

A Pat. No. 5,187,611 to White et al., shows a system which illuminates an object while avoiding reflection and glare.

Pat Nos. 4,733,926 to Title; 5,548,427 to May and 5,402,260 to Tsuneda et al. were also identified.

It is specifically noted that a Combination system of a dual wire grid polarizer in combination with compensators), (particularly In the context of an IR Ellipsometer/Polarimeter system), was not found.

Optical elements providing Polarizer and Retarder system characteristics which approach ideal over even some limited spectral range, it should be appreciated, would provide utility. The present invention provides advancement toward the goal of achieving ideal optical Polarizer and Retarder system elements which demonstrate acceptably ideal behavior over relatively large wavelength ranges.

DISCLOSURE OF THE INVENTION

For general insight it is first noted that polarimeter systems serve to monitor polarization states in a beam of electromagnetic radiation, and ellipsometer systems serve to measure change in polarization state in a beam of electromagnetic radiation, which change results from interaction of said beam of electromagnetic with a sample system.

Polarizer and Retarder/Compensator Optical Elements are commonly present components in Ellipsometer and Polarimeter systems. Ideally, Polarizers accept electromagnetic radiation in a less than linear polarization state and provide it in a linearly polarized state, and Retarder/Compensator components receive polarized electromagnetic radiation and impose angular retardation between orthogonal components therein.

Generally, an ellipsometer/polarimeter system typically comprises in sequence:

a source of electromagnetic radiation;

a polarizer;

a compensator;

an analyzer; and a detector system;

and the present invention comprises novel Polarizer and Compensator designs.

The present invention Polarizer system comprises first and second wire grid polarizers which each have fast axes of polarization. Said fast axes of polarization are oriented with their directions of polarization essentially parallel to one another and said first and second wire grid polarizers each present with first and second essentially parallel sides. Said first and second wire grid polarizers are oriented, as viewed in side elevation, with first and second sides of one wire grid polarizer oriented other than parallel to first and second sides of the other wire grid polarizer. In use a beam of electromagnetic radiation is caused to impinge upon one of said first and second wire grid polarizers on one side thereof, partially reflect therefrom and partially transmit therethrough. This is followed by said transmitted beam of electromagnetic radiation being caused to impinge upon the other wire grid polarizer on one side thereof, partially reflect therefrom and partially transmit therethrough, such that a beam of electromagnetic radiation passing through both of said first and second wire grid polarizers emerges from the second thereof in a polarized state in a propagation direction which is essentially undeviated and undisplaced from the incident beam of electromagnetic radiation. An important aspect of the present invention polarizer system design is that the resulting reflected electromagnetic beam portions are directed away from said emerging polarized beam of electromagnetic radiation. It is noted that, while not a limitation, said present invention Polarizer is particularly applicable to in infrared range electromagnetic radiation The present invention, in addition to providing a new design for a Polarizer system, provides a number of new Retarder/Compensator system designs. Before describing said new Retarder/Compensator system designs, however, it is of benefit to realize that an ideal Retarder/Compensator would provide a constant amount of retardation between orthogonal components in a beam of electromagnetic radiation regardless of how said beam of electromagnetic radiation is caused to be incident upon said Retarder/Compensator, and regardless of the wavelength of the electromagnetic radiation present. As well, an ideal Retarder/Compensator system would not preferentially effect the magnitude of either orthogonal component in a beam of polarized electromagnetic radiation caused to pass therethrough. In addition, the direction of propagation of a beam of electromagnetic radiation should not be changed by passage through an ideal Retarder/Compensator and passage through an ideal Retarder/Compensator should not introduce a displacement or "offset" of said beam of electromagnetic radiation. Such should be the case even where said Retarder/Compensator is caused to continuously rotate during use, as in a Rotating Compensator Ellipsometer system.

Description of retarder designs, any of which can be utilized in combination with said present invention Polarizer system in a polarimeter/ellipsometer system, follow directly.

The first retarder system comprises a first triangular shaped element, which as viewed in side elevation presents with first and second sides which project to the left and right and downward from an upper point. Said first triangular shaped element first and second sides have reflective outer surfaces, and can have metal coated thereon to increase reflectivity. Said retarder system further comprises a second triangular shaped element which, as viewed in side elevation, presents with first and second sides which project to the left and right and downward from an upper point, said second triangular shaped element being made of material which provides internal reflective interfaces on first and second sides inside thereof, which internal reflectivity can be enhanced by a coating applied to the outer surfaces thereof. Said second triangular shaped element is typically made of a material with an index of refraction which is greater that the surrounding ambient. Said second triangular shaped element is oriented with respect to the first triangular shaped element such that the upper point of said second element is oriented essentially vertically directly above the upper point of said first element. In use an input electromagnetic beam of radiation caused to approach one of said first and second sides of said first triangular shaped element along an essentially horizontally oriented locus, is caused to externally reflect from an outer surface thereof and travel along a locus which is essentially upwardly vertically oriented. Next said electromagnetic beam of radiation is caused to enter said second triangular shaped element and essentially totally internally reflect from one of said first and second sides thereof, then proceed along an essentially horizontal locus and essentially totally internally reflect from the other of said first and second sides and proceed along an essentially downward vertically oriented locus. This is followed by an external reflection from the other of said first and second sides of said first triangular shaped elements such that said electromagnetic beam of radiation proceeds along an essentially horizontally oriented locus undeviated and undisplaced from the essentially horizontally oriented locus of said input beam of essentially horizontally oriented electromagnetic radiation. This is the case even when said retarder system is caused to rotate. The result of said described retarder system application being that retardation is entered between orthogonal components of said input electromagnetic beam of radiation. Of course, and as applies to all optical elements described in this Disclosure, the entire retarder system could be rotated in space such that horizontal and vertical are replaced with angles with respect to horizontal and vertical, however, the relative relationships of the first and second triangular shaped elements etc. would remain constant as would the operational aspects of said retarder system. That is, horizontal and vertical are utilized only as a convenience to describing the geometry of the retarder systems herein.

The second retarder system comprises a parallelogram shaped element which, as viewed in side elevation, has top and bottom sides parallel to one another, both said top and bottom sides being oriented essentially horizontally. Said retarder system also has right and left sides parallel to one another, both said right and left sides being oriented at an angle to horizontal. Said retarder system is made of a material with an index of refraction greater than that of a surrounding ambient. In use an input beam of electromagnetic radiation caused to enter a side of said retarder selected from the group consisting of: (right and left), along an essentially horizontally oriented locus, is caused to be diffracted inside said retarder and follow a locus which causes it to essentially totally internally reflect from internal interfaces of both said top and bottom sides, and emerge from said retarder from a side selected from the group consisting of (left and right respectively), along an essentially horizontally oriented locus which is undeviated and undisplaced from the essentially horizontally oriented locus of said input beam of essentially horizontally oriented electromagnetic radiation. This is the case even when said retarder system is caused to rotate. The result of said described retarder system application being that retardation is entered between orthogonal components of said input electromagnetic beam of radiation.

The third retarder system comprises first and second triangular shaped elements. Said first triangular shaped element, as viewed in side elevation, presents with first and second sides which project to the left and right and downward from an upper point, said first triangular shaped element further comprising a third side which is oriented essentially horizontally and which is continuous with, and present below said first and second sides. Said second triangular shaped element, as viewed in side elevation, presents with first and second sides which project to the left and right and upward from a lower point, said second triangular shaped element further comprising a third side which is oriented essentially horizontally and which is continuous with, and present above said first and second sides. Said first and second triangular shaped elements being positioned so that a rightmost side of one of said first and second triangular shaped elements is in contact with a leftmost side of the other of said first and second triangular shaped elements over at least a portion of the lengths thereof. Said first and second triangular shaped elements are each made of material with an index of refraction greater than that of a surrounding ambient. In use an input beam of electromagnetic radiation caused to enter a side of a triangular shaped element selected from the group consisting of: (first and second), which is not in contact with said other triangular shape element, then is caused to diffracted inside said retarder and follow a locus which causes it to essentially totally internally reflect from internal interfaces of said third sides of each of said first and second triangular shaped elements, and emerge from a side of said triangular shaped element selected from the group consisting of: (second and first), not in contact with said other triangular shape element, along an essentially horizontally oriented locus which is undeviated and undisplaced from the essentially horizontally oriented locus of said input beam of essentially horizontally oriented electromagnetic radiation. This is the case even when said retarder system is caused to rotate. The result of said described retarder system application being that retardation is entered between orthogonal components of said input electromagnetic beam of radiation.

The forth retarder system comprises a triangular shaped element, which as viewed in side elevation presents with first and second sides which project to the left and right and downward from an upper point. Said retarder system further comprises a third side which is oriented essentially horizontally and which is continuous with, and present below said first and second sides. Said retarder system is made of a material with an index of refraction greater than that of a surrounding ambient. In use an input beam of electromagnetic radiation caused to enter a side of said retarder selected from the group consisting of: (first and second), along an essentially horizontally oriented locus, is caused to diffracted inside said retarder and follow a locus which causes it to essentially totally internally reflect from internal interface of said third side, and emerge from said retarder from a side selected from the group consisting of (second and first respectively), along an essentially horizontally oriented locus which is undeviated and undisplaced from the essentially horizontally oriented locus of said input beam of essentially horizontally oriented electromagnetic radiation. This is the case even when said retarder system is caused to rotate. The result of said described retarder system application being that retardation is entered between orthogonal components of said input electromagnetic beam of radiation.

The fifth retarder system comprises first and second parallelogram shaped elements which, as viewed in side elevation, each have top and bottom sides parallel to one another, both said top and bottom sides being oriented at an angle to horizontal. Said first and second parallelogram shaped elements also have right and left sides parallel to one another, both said right and left sides being oriented essentially vertically. Said retarders are made of material with an index of refraction greater than that of a surrounding ambient. A right most vertically oriented side of one of said first and second parallelograms is in contact with a leftmost vertically oriented side of the other of said first and second parallelogram shaped elements. In use an input beam of electromagnetic radiation caused to enter an essentially vertically oriented side of said first parallelogram shaped element which is not in contact with an essentially vertically oriented side of said second parallellogram shaped element, along an essentially horizontally oriented locus, is caused to diffracted inside said retarder system and follow a locus which causes it to essentially totally internally reflect from internal interfaces of both said top and bottom sides of both said first and second parallelogram shaped elements, then emerge from a side of said second parallelogram shaped element not in contact with an essentially vertically oriented side of said first parallelogram shaped element, along an essentially horizontally oriented locus which is undeviated and undisplaced from the essentially horizontally oriented locus of said input beam of essentially horizontally oriented electromagnetic radiation. This is the case even when said retarder system is caused to rotate. The result of said described retarder system application being that retardation is entered between orthogonal components of said input electromagnetic beam of radiation.

The sixth retarder system comprises first and second Berek-type retarders which each have an optical axes essentially perpendicular to a surface thereof. Each of said first and second Berek-type retarders has a fast axis which fast axes are oriented in an orientation selected from the group consisting of: (parallel to one another and other than parallel to one another). Said first and second Berek-type retarders each present with first and second essentially parallel sides. Said first and second Berek-type retarders are oriented, as viewed in side elevation, with first and second sides of one Berek-type retarder being oriented other than parallel to first and second sides of the other Berek-type retarder. In use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a direction which is essentially undeviated and undisplaced from the incident beam of electromagnetic radiation. This is the case even when said retarder system is caused to rotate. The result of said described retarder system application being that retardation is entered between orthogonal components of said input electromagnetic beam of radiation.

The seventh retarder system comprises first and second Berek-type retarders which each have an optical axes essentially perpendicular to a surface thereof, each of which first and second Berek-type retarders has a fast axis, said fast axes in said first and second Berek-type retarders being oriented other than parallel to one another. Said first and second Berek-type retarders each present with first and second essentially parallel sides. Said first and second Berek-type retarders are oriented, as viewed in side elevation, with first and second sides of one Berek-type retarder being oriented other than parallel to first and second sides of the other Berek-type retarder. In use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a direction which is an essentially undeviated and undisplaced from the incident beam of electromagnetic radiation. Said seventh retarder system further comprises third and forth Berek-type retarders which each have an optical axes essentially perpendicular to a surface thereof, each of which third and forth Berek-type retarders has a fast axis, said fast axes in said third and forth Berek-type retarders being oriented other than parallel to one another. Said third and forth Berek-type retarders each presenting with first and second essentially parallel sides, and said third and forth Berek-type retarders are oriented, as viewed in side elevation, with first and second sides of one of said third and forth Berek-type retarders being oriented other than parallel to first and second sides of said forth Berek-type retarder. In use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is an essentially undeviated and undisplaced from said incident beam of electromagnetic radiation. This is the case even when said retarder system is caused to rotate. The result of said described retarder system application being that retardation is entered between orthogonal components of said input electromagnetic beam of radiation.

The eighth retarder system comprises first, second, third and forth Berek-type retarders which each have an optical axes essentially perpendicular to a surface thereof, each of which first and second Berek-type retarders has a fast axis, said fast axes in said first and second Berek-type retarders being oriented essentially parallel to one another. Said first and second Berek-type retarders each present with first and second essentially parallel sides, and said first and second Berek-type retarders are oriented, as viewed in side elevation, with first and second sides of one Berek-type retarder being oriented other than parallel to first and second sides of the other Berek-type retarder. In use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a direction which is an essentially undeviated and undisplaced from the incident beam of electromagnetic radiation. Each of which third and forth Berek-type retarders also has a fast axis, and said fast axes in said third and forth Berek-type retarders are oriented essentially parallel to one another but other than parallel to the fast axes of said first and second Berek-type retarders. Said third and forth Berek-type retarders each present with first and second essentially parallel sides, and said third and forth Berek-type retarders are oriented, as viewed in side elevation, with first and second sides of one of said third and forth Berek-type retarders being oriented other than parallel to first and second sides of said forth Berek-type retarder. In use an incident beam of electromagnetic radiation, which is that beam of electromagnetic radiation exiting said second Berek-type retarder, is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is an essentially undeviated and undisplaced from said incident beam of electromagnetic radiation. This is the case even when said retarder system is caused to rotate. The result of said described retarder system application being that retardation is entered between orthogonal components of said input electromagnetic beam of radiation.

A ninth, (class of), retarder system variation can be comprised of two Berek-type plate pairs, wherein the fast axes of the various Berek-type plates are all different, or wherein the fast axes of the first two Berek-type plates are different but the second two Berek-type plates have fast axes oriented parallel to one another etc.

As alluded to, the present invention can comprise the present invention dual wire grid polarizer in functional combination with any of the recited retarder systems. Said combinations are all unique in view of known prior art, and all said combinations can provide excellent electromagnetic beam polarization and retardation control, without introducing deviation or displacement into said beam of electromagnetic radiation which is caused to transmit therethrough, even where said retarder is caused to continuously rotate in use. This is true over a large range of wavelengths, including in the infrared.

The present invention will be better understood by reference to the Detailed Description Section of this Disclosure in combination with the accompanying drawings.

SUMMARY OF THE INVENTION

It is therefore a purpose of the present invention to provide polarizer and retarder system optical elements for use in ellipsometer/polarimeter systems.

It is another purpose of the present invention to provide polarizer systems with high extinction ratios which can be used at infrared wavelengths.

It is yet another purpose of the present invention to provide retarder systems with retardation vs. wavelength dispersion characteristics within a range of acceptability.

It is still yet another purpose of the present invention to provide optical elements do not introduce significant deviation and/or displacement into the propagation direction of a beam of electromagnetic radiation caused to interact therewith, even when said optical element is caused to continuously rotate.

It is yet still another purpose of the present invention to provide optical elements which demonstrate limited immunity to beam alignment changes.

It is another purpose of the present invention to provide a retarder system which enters a phase retardation between orthogonal components of polarized electromagnetic radiation without greatly, preferentially, modifying the intensity of either orthogonal component thereof.

It is yet another purpose of the present invention to provide optical elements which do not exhibit large sensitivity of extinction ratio or retardence entered between orthogonal components of an electromagnetic beam of radiation caused to interact therewith, as a function of beam alignment with respect thereto.

It is still yet another purpose of the present invention to provide optical elements which are easy to fabricate and that fabrication be from easily obtainable materials.

BRIEF DESCRIPTION OF THE DRAWINGS

FIG. 8b shows a possible relationship between fast axes of Berek-type plates in the FIG. 9a retarder system.

FIG. 10b shows actual measured retardation results for a prototype dual plate Berek-type retarder system as in FIG. 8a.

DETAILED DESCRIPTION

Figure 1:
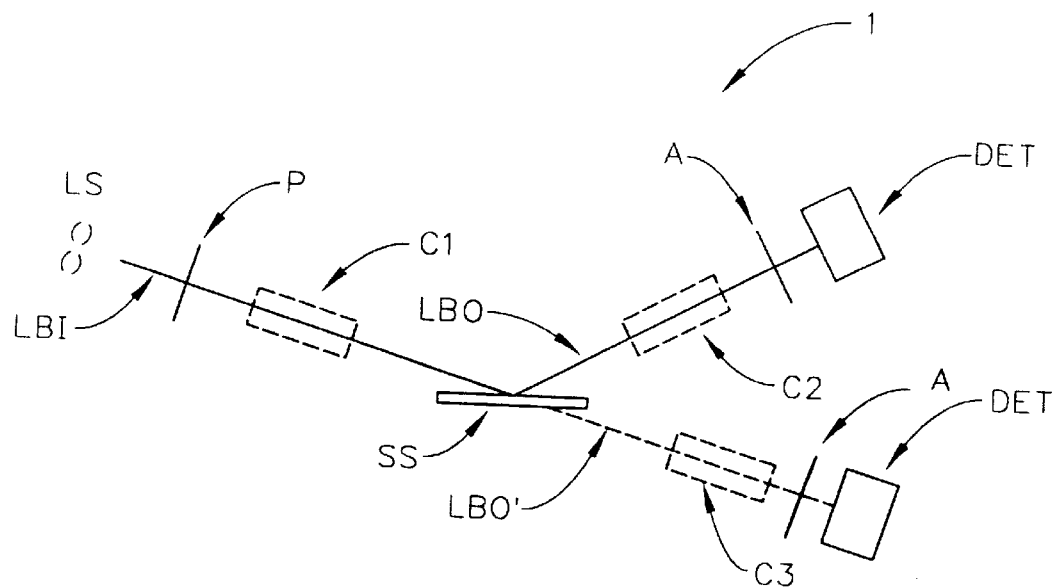
FIG. 1 shows a general diagram of an ellipsometer system.

Turning now to the Drawings, there is diagramatically shown in FIG. 1 a general ellipsometer system (1). Shown in functional sequence are:

a source of electromagnetic radiation (LS);

a polarizer (P);

at least one compensator (C1) (C2) (C3);

an analyzer (A); and a detector system (DET);

where said polarizer, compensator and analyzer can each be variously, stationary, rotatable or rotating in use.

FIG. 1 shows that a beam of electromagnetic radiation (LBI), (after interaction with said Polarizer (P) and if present compensator (C1)), is caused to interact with a sample system (SS) and either reflect off thereof (LBO), or be transmitted therethrough (LBO') said sample system (SS) and enter a Detector (DET). Multiple compensators (C1) (C2) and (C3) are shown in dashed lines to indicate that only one, or more than one can be present.

The present invention provides new polarizer (P) and compensator (C1) (C2) (C3) components which are directly applicable to use in the FIG. 1 system.

Figure 2A:
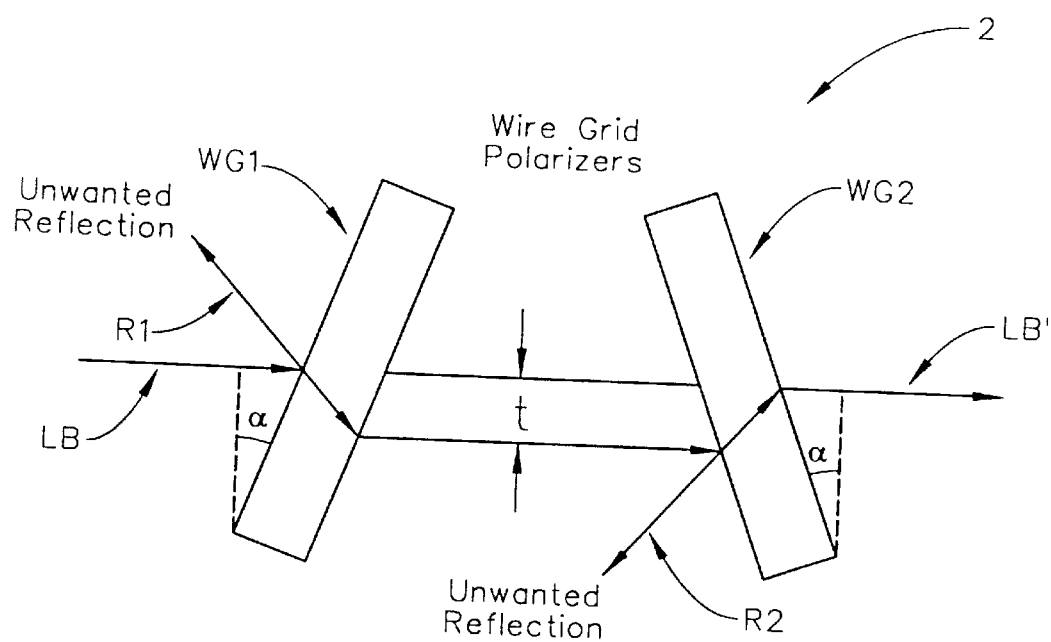
FIG. 2a shows a dual wire grid polarizer system.
Figure 2B:
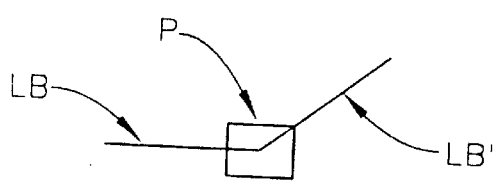
FIG. 2b demonstrates deviation in the propagation direction of a beam of electromagnetic radiation caused by interaction with an optical element.
Figure 2C:
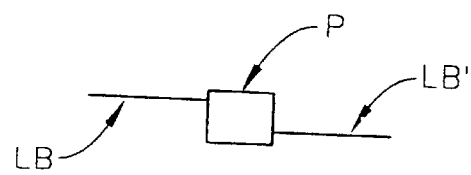
FIG. 2c demonstrates displacement in the propagation direction of a beam of electromagnetic radiation caused by interaction with an optical element.

FIG. 2a shows that the present invention Polarizer system (2) comprises first (WG1) and second (WG2) wire grid polarizers which each have fast axes of polarization. Said fast axes of polarization are oriented with their directions of polarization essentially parallel to one another and said first and second wire grid polarizers each present with first and second essentially parallel sides. Said first (WG1) and second (WG2) wire grid polarizers are oriented, as viewed in side elevation, with first and second sides of one wire grid polarizer oriented other than parallel to first and second sides of the other wire grid polarizer. Angle alpha (α) and alpha' (α') are shown to identify this relationship. Alpha is not a critical angle, but must be large enough to divert reflections (R1) (R2) away from interfering with input and output beams of electromagnetic radiation (LB) and (LB'), and it has been found that alpha (α) and alpha' (α') values of ten (10) degrees each generally works well. An input beam of electromagnetic radiation (LB) is shown as being caused to impinge upon said first (WG1) wire grid polarizer on one side thereof, partially reflect therefrom and partially transmit therethrough. (Said beam of electromagnetic radiation would correspond to (LBI) in FIG. 1). This is followed by said beam of electromagnetic radiation being caused to impinge upon the other wire grid (WG2) polarizer on one side thereof, partially reflect therefrom and partially transmit therethrough, such that a beam of electromagnetic radiation passing through both of said first (WG1) and second (WG2) wire grid polarizers emerges from the second (WG2) thereof in a polarized state, (identified as (LB'), in a direction which is an essentially undeviated and undisplaced from the incident beam of electromagnetic radiation. To aide understanding, FIG. 2b is included to demonstrate a "deviated" (LB') as compared to (LB). It should be appreciated then that the term "deviated" indicates that a change in propagation direction of a beam of electromagnetic radiation. FIG. 2c is included to demonstrate a "displacement" in a beam of electromagnetic radiation. In addition to causing essentially no deviation or displacement in a beam of electromagnetic radiation caused to interact therewith, an important aspect of the present invention polarizer system design is that the resulting reflected electromagnetic beam portions (R1) (R2) are directed away from said emerging polarized beam of electromagnetic radiation (LB'). Note that an identifier (t) is included in FIG. 2a to show the effects of different effective refractive index in said Wire Grid Polarizers (WG1) and (WG2) as compared to the surrounding ambient. Note that the second Wire Grid Polarizer (WG2) effectively cancels the effect of the first Wire Grid Polarizer (WG1) such that essentially no displacement exists between input (LB) and output (LB') electromagnetic beams in FIG. 2a, as canceling, oppositely directed, displacements of magnitude (t) are entered by each of (WG1) and (WG2). It is also noted that the sequential presence of two Polarizers, (WG1) and (WG2) leads to an overall Polarizer system (2) which has a high extinction ratio, (ie. a highly linearly polarized beam of electromagnetic radiation exits therefrom).

Figure 3:
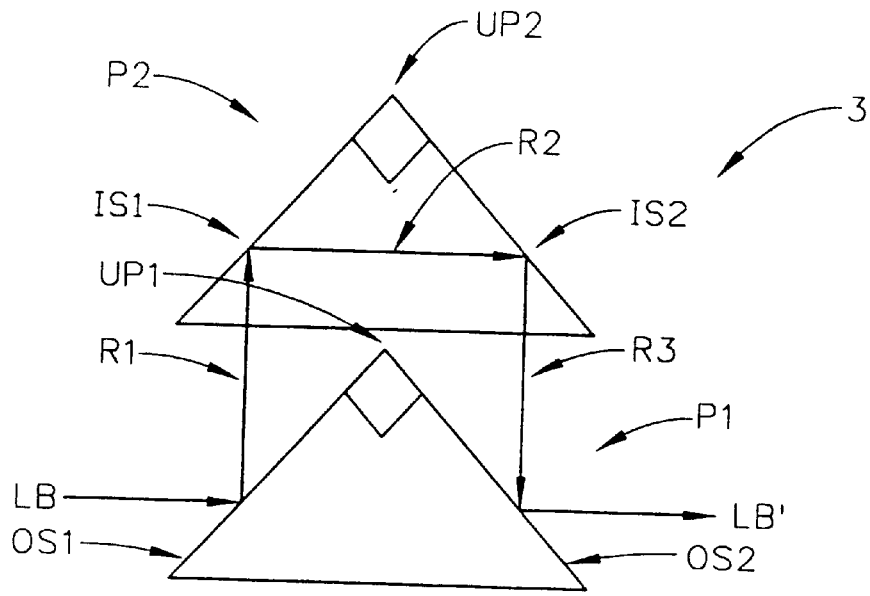
FIG. 3 shows a present invention retarder system constructed utilizing two triangular shape elements.

FIG. 3 shows that the first present invention retarder system (3) comprises a first triangular shaped element (P1), which as viewed in side elevation presents with first (OS1) and second (OS2) sides which project to the left and right and downward from an upper point (UP1). Said first triangular shaped element (P1) first (OS1) and second (OS2) sides have reflective outer surfaces. Said retarder system (3) further comprises a second triangular shaped element (P2) which as viewed in side elevation presents with first (IS1) and second (IS2) sides which project to the left and right and downward from an upper point (UP2), said second triangular shaped element (P2) being made of material which provides internally reflective, phase delay introducing, interfaces on first (IS1) and second (IS2) sides inside thereof. Said second triangular shaped element (P2) is oriented with respect to the first triangular shaped element (P1) such that the upper point (UP2) of said second triangular shaped element (P2) is oriented essentially vertically directly above the upper point (UP1) of said first triangular shaped element (P1). In use an input electromagnetic beam of radiation (LB) caused to approach said first (OS1) side of said first triangular shaped element (P1) along an essentially horizontally oriented locus, is shown as being caused to externally reflect from an outer surface thereof and travel along as electromagnetic beam of radiation (R1) which is essentially upwardly vertically oriented. Next said electromagnetic beam of radiation (R1) is caused to enter said second triangular shaped element (P2) and essentially totally internally reflect from said first (IS1) side thereof, then proceed along an essentially horizontal locus and essentially totally internally reflect from the second (IS2) side thereof and proceed along an essentially downward vertically oriented electromagnetic beam of radiation (R3). This is followed by an external reflection from an outer surface of said second side (OS2) of said first triangular shaped element (P1) such that said electromagnetic beam (LB') of radiation proceeds along an essentially horizontally oriented locus, undeviated and undisplaced from the essentially horizontally oriented locus of said input beam (LB) of essentially horizontally oriented electromagnetic radiation. This is the case even when said retarder system (3) is caused to rotate. The result of said described retarder system (3) application being that retardation is entered between orthogonal components of said input electromagnetic beam of radiation (LB). Further, said first (P1) and second (P2) triangular shaped elements are typically right triangles in side elevation as shown in FIG. 3, and the outer surfaces of first (OS1) and second (OS2) sides are typically, but not necessarily, made reflective by the presence of a coating of metal thereupon. A coating of metal serves assure a high reflectance and good electromagnetic beam radiation intensity throughput. Also, assuming accurately manufactured right angle first (P1) and second (P2) triangular shaped elements are utilized, this compensator design provides inherent compensation of both angular and translational misalignments of the input light beam (LB). As well, the total retardence provided is compensated for angular misalignments of the input electromagnetic radiation beam. That is, if the input electromagnetic radiation beam (LB) is not aligned so as to form an angle of incidence of forty-five (45) degrees with the first outer surface (OS1), the reflected electromagnetic beam (R1) will internally reflect at the first internal surface (IS1) of the second triangular shaped element (P2) at a larger (smaller) angle than would be the case if said angle of Incidence were forty-five (45) degrees. This effect, however, is directly compensated by a smaller (larger) angle of incidence of electromagnetic beam (R2) where it internally reflects from inner surface (IS2) of the second triangular shaped element (P2). As another comment it is to be understood that because of the oblique angles of incidence of the reflections from the outer surfaces (OS1) and (OS2) of the first triangular shaped element (P1) a polarimeter/ellipsometer in which said compensator (3) is present will require calibration to characterize the PSI-like component thereof.

Figure 4:
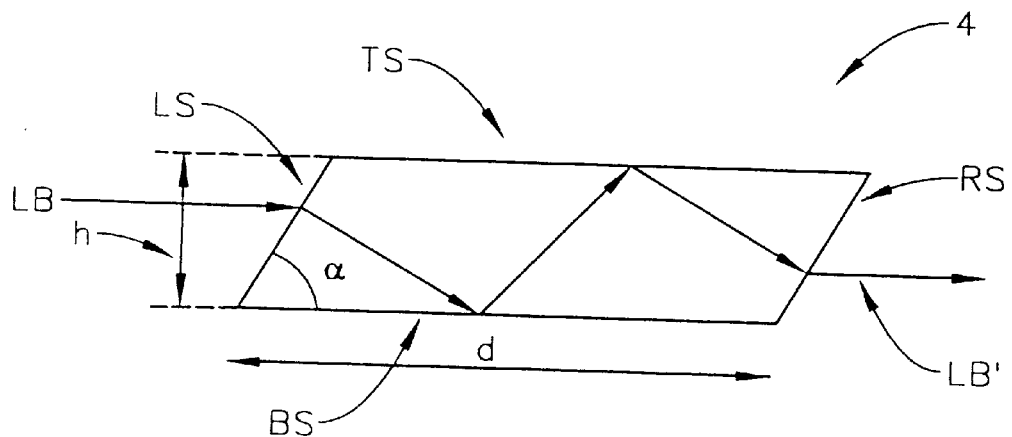
FIG. 4 shows a present invention retarder system consisting of a parallellogram shaped element.

FIG. 4 shows that the second present invention retarder system (4) comprises a parallelogram shaped element which, as viewed in side elevation, has top (TS) and bottom sides (BS), each of length (d) parallel to one another, both said top (TS) and bottom (NS) sides being oriented essentially horizontally. Said retarder system (4) also has right (RS) and left (LS) sides parallel to one another, both said right (RS) and left (LS) sides being of length (d/cos(α)), where alpha (α) is shown as an angle at which said right (RS) and left (LS) sides project from horizontal. Said retarder system (4) is made of a material with an index of refraction greater than that of a surrounding ambient. In use an input beam of electromagnetic radiation (LB) caused to enter the left side (LS) of said retarder system (4), along an essentially horizontally oriented locus, is caused to diffracted inside said retarder system (4) and follow a locus which causes it to essentially totally internally reflect from internal interfaces of both said top (TS) and bottom (BS) sides, and emerge from said retarder system (4) as (LB') from the right side (RS) thereof, along an essentially horizontally oriented locus which is undeviated and undisplaced from the essentially horizontally oriented locus of said input beam (LB) of essentially horizontally oriented electromagnetic radiation. This is the case even when said retarder system (4) is caused to rotate. The result of said described retarder system (4) application being that retardation is entered between orthogonal components of said input electromagnetic beam of radiation at said internal reflections from the top (TS) and bottom (BS) surfaces. This retarder system is very robust as it is made of single piece construction. It is noted that adjustment of the angle alpha (α) in manufacture allows setting the amount of retardation which is provided by the retarder system (4). In addition, coatings can be externally applied to top (TS) and bottom surface (BS) to adjust retardation effected by internal reflection from said top (TS) and bottom (BS) surfaces. A formula is included in FIG. 4 which defines the retardation provided thereby, said formula being:

$$\frac{d}{h} = 2 \cdot \tan(\phi), \text{ where } \phi = \alpha + \sin^{-1}\left(\frac{\sin(90-\alpha)}{n}\right)$$

Figure 5:
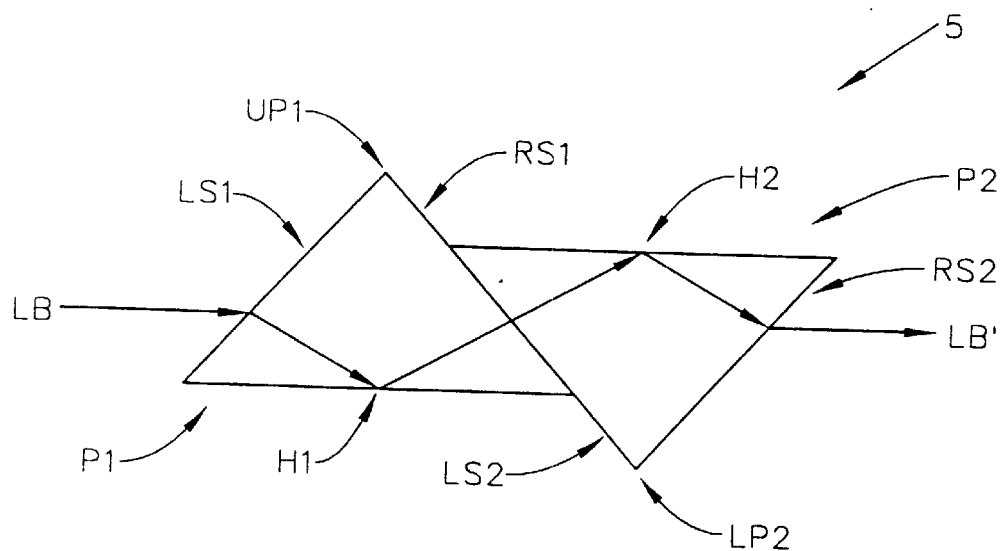
FIG. 5 shows another present invention retarder system constructed utilizing two triangular shape elements.

FIG. 5 shows that the third present invention retarder system (5) comprises first (P1) and second (P2) triangular shaped elements. Said first (P1) triangular shaped element, as viewed in side elevation, presents with first (LS1) and second (RS1) sides which project to the left and right and downward from an upper point (UP1), said first triangular shaped element (P1) further comprising a third side (H1) which is oriented essentially horizontally and which is continuous with, and present below said first (LS1) and second (RS1) sides. Said second triangular shaped element (P2), as viewed in side elevation, presents with first (LS2) and second (RS2) sides which project to the left and right and upward from a lower point (LP2), said second triangular shaped element (P2) further comprising a third side (H2) which is oriented essentially horizontally and which is continuous with, and present above said first (LS2) and second (RS2) sides. Said first (P1) and second (P2) triangular shaped elements being positioned so that a rightmost side (RS1) of said first (P1) triangular shaped element is in contact with a leftmost side (LS2) of said second (P2) triangular shaped element over at least a portion of the lengths thereof. Said first (P1) and second (P2) triangular shaped elements are each made of material with an index of refraction greater than that of a surrounding ambient. In use an input beam (LB) of electromagnetic radiation caused to enter the left (LS1) side of said first (P1) triangular shaped element and is caused to diffracted inside said retarder system (5) and follow a locus which causes it to essentially totally internally reflect from internal interfaces of said third sides (H1) and (H2) of said first (P1) and second (P2) triangular shaped elements, respectively, and emerge from said right side (RS2) of said second (P2) triangular shaped element as electromagnetic radiation beam (LB') which is oriented along an essentially horizontal locus which is undeviated and undisplaced from the essentially horizontally oriented locus of said input beam (LB) of essentially horizontally oriented electromagnetic radiation. This is the case even when said retarder system (5) is caused to rotate. The result of said described retarder system (5) application being that retardation is entered between orthogonal components of said input electromagnetic beam of radiation (LB). It is noted that as long as the third sides (H1) and (H2) of said first (P1) and second (P2) triangular shaped elements are parallel, the output electromagnetic beam (LB') is undeviated and undisplaced from the input electromagnetic beam (LB) in use. It is noted that The triangular shape elements (P1) and/or (P2) can be made of various materials with various indicies of refraction, and coating(s) can be applied to one or both of the third sides (H1) and (H2) of said first (P1) and second (P2) triangular shaped elements to adjust retardation entered to an electromagnetic beam (LB1).

Figure 6A:
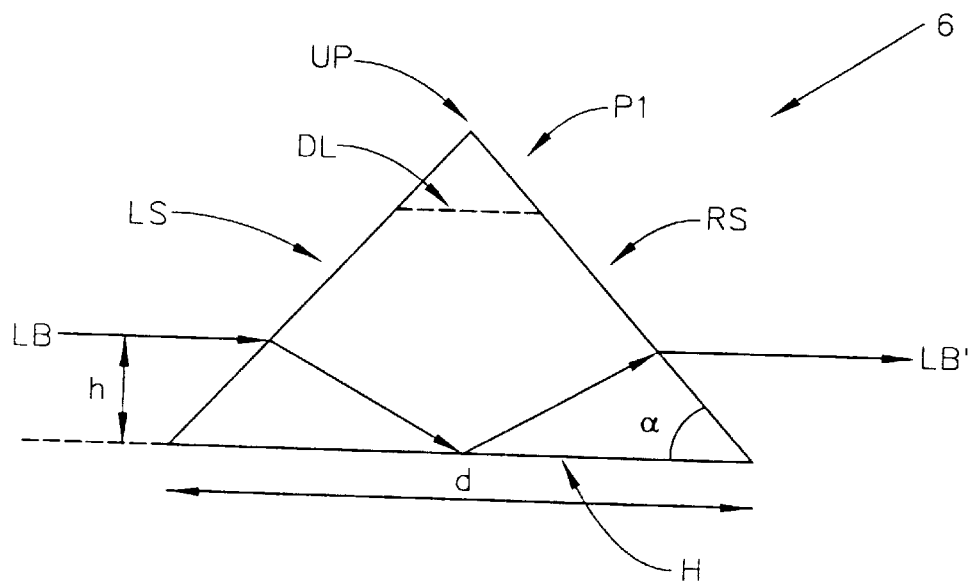
FIG. 6a shows another present invention retarder system consisting of a triangular shaped element.
Figure 6B:
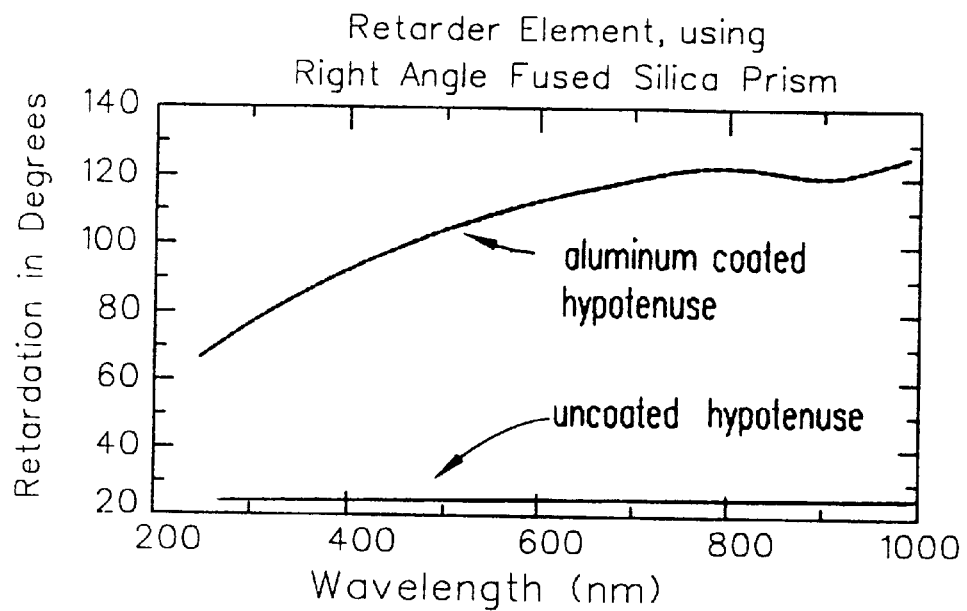
FIG. 6b shows the retardation vs. wavelength characteristics for the retarder system of FIG. 6a for the cases of uncoated and metal coated external surfaces at sides thereof which effect internal reflections.

FIG. 6A shows that the forth present invention retarder system (6) comprises a triangular shaped element, which as viewed in side elevation presents with first (LS) and second (RS) sides which project to the left and right and downward from an upper point (UP). Said retarder system (6) further comprises a third side (H) which is oriented essentially horizontally and which is continuous with, and present below said first (LS) and second (RS) sides. Said retarder system (6) is made of a material with an index of refraction greater than that of a surrounding ambient. In use an input beam of electromagnetic radiation (LB) caused to enter the first (LS) side of said retarder system (6) along an essentially horizontally oriented locus, is caused to diffracted inside said retarder system (6) and follow a locus which causes it to essentially totally internally reflect from internal interface of said third (H) side, and emerge from said retarder system (6) from the second (RS) side along an essentially horizontally oriented locus which is undeviated and undisplaced from the essentially horizontally oriented locus of said input beam of essentially horizontally oriented electromagnetic radiation (LB). This is the case even when said retarder system (6) is caused to rotate. The result of said described retarder system (6) application being that retardation is entered between orthogonal components of said input electromagnetic beam of radiation (LB). The FIG. 6a retarder system (6) is typically an isosceles prism which is available off-the-shelf with an angle alpha (α) of forty-five (45) degrees. As long as the input electromagnetic beam (LB) height (h) is chosen in accordance with the formula included in FIG. 6a and repeated below:

$$d = 2h\left(\frac{1}{\tan(\alpha)} + \tan(\phi)\right), \text{ where } \phi = \alpha + \sin^{-1}\left(\frac{\sin(90-\alpha)}{n}\right)$$

in conjunction with the index of refraction (n) of the material from which the FIG. 6a retarder system (6) is made, and the locus of the input electromagnetic radiation beam (LB) is parallel with the third side (H) of said retarder system (6), the output electromagnetic beam (LB') will not be deviated or translated with respect to the input electromagnetic beam (LB). As well, note the dashed line (DL) below the upper point (UP). This indicates that as the region above said dashed line (DL) is not utilized, the portion of said retarder system (6) thereabove can be removed. It is also noted that the input electromagnetic beam (LB) enters and exits the retarder system (6) other than along a normal to a surface thereof, said retarder system is not an ideal retarder with a PSI of forty-five (45) degrees. It is noted that the third side (H) of the retarder system (6) can be coated to change the retardation effects of an internal reflection of an electromagnetic beam of radiation therefrom, and such a coating can have an adverse effect on the nonideal PSI characteristics. FIG. 6b shows another effect of coating the third side (H) of a FIG. 6a right angle prism retarder system (6) which is made of fused silica, with aluminum. The solid line in the FIG. 6b plot shows an essentially constant retardation, with respect to wavelength, is caused by an internal reflection from a third side (H) which is not coated, and that a varying, but generally larger retardation is caused in an electromagnetic radiation beam by reflection from a third side (H) of a retarder system (6) which is coated with aluminum. It is noted, however, that the spectral variation of retardence demonstrated by an aluminum coated third side of a retarder system (6) is within acceptable limits for most ellipsometer applications.

Figure 7:
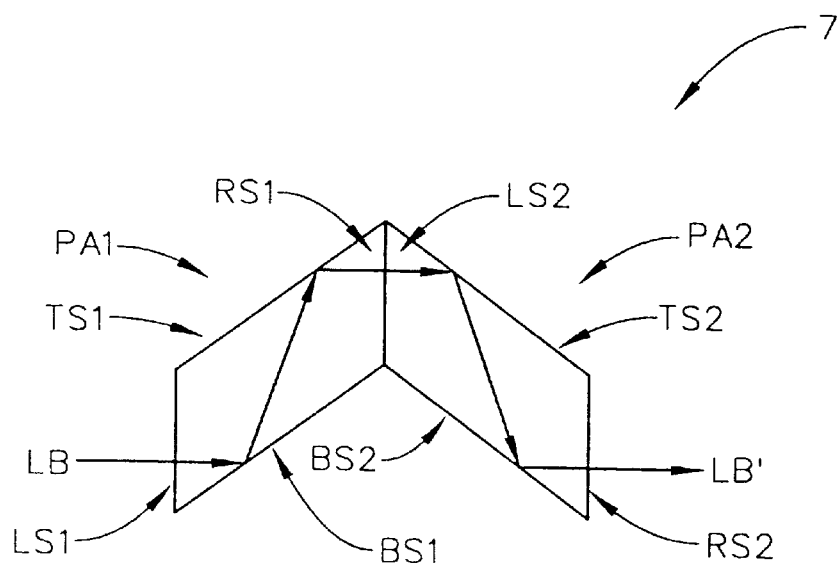
FIG. 7 shows a present invention retarder system consisting of two parallellogram shaped elements.

FIG. 7 shows that the fifth present invention retarder system (7) comprises first (PA1) and second (PA2) parallelogram shaped elements which, as viewed in side elevation, each have top (TS1)/(TS2) and bottom (BS1)/(BS2) sides parallel to one another, both said top (TS1) (TS2) and bottom (BS1) (BS2) sides each being oriented at an angle to horizontal. Said first (PA1) and second (PA2) parallelogram shaped elements also each have right (RS1)/(RS2) and left (LS1)/(LS2) sides parallel to one another, all said right (RS1) (RS2) and left (LS1) (LS2) sides being oriented essentially vertically. Said first (PA1) and second (PA2) parallelogram shaped elements are made of material with an index of refraction greater than that of a surrounding ambient. A right most vertically oriented side (RS1) of said first parallelogram is in contact with a leftmost (LS2) vertically oriented side of the second parallelogram shaped element (PA2). In use an input beam of electromagnetic radiation (LB) caused to enter an essentially vertically oriented left side (LS1) of said first parallelogram shaped element (PA1) along an essentially horizontally oriented locus, is caused to be diffracted inside said retarder system and follow a locus which causes it to essentially totally internally reflect from internal interfaces of both said top (TS1) (TS2) and bottom (BS1) (BS2) sides of both said first and second parallelogram shaped elements (PA1) (PA2), then emerge from a right side (RS2) of said second parallelogram shaped element (PA2) along an essentially horizontally oriented locus as output beam of electromagnetic radiation (LB') which is undeviated and undisplaced from the essentially horizontally oriented locus of said input beam of essentially horizontally oriented electromagnetic radiation (LB). This is the case even when said retarder system (7) is caused to rotate. The result of said described retarder system (7) application being that retardation is entered between orthogonal components of said input electromagnetic beam of radiation (LB).

Figure 8A:
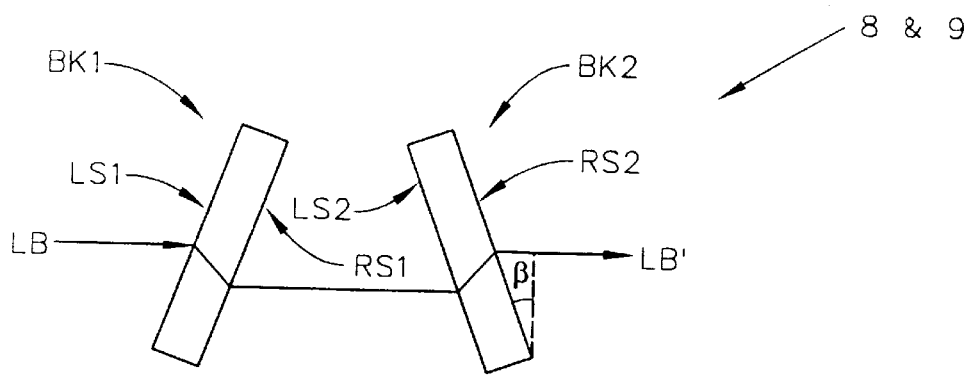
FIG. 8a shows a dual Berek-type plate retarder system.
Figure 8B:
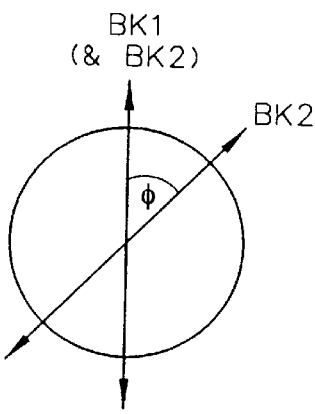
FIG. 8b shows a possible relationship between fast axes of the Berek-type plates in the FIG. 8a retarder system.

FIG. 8a shows that the sixth present invention retarder system (8) comprises first (BK1) and second (BK2) Berek-type retarders which each have an optical axes essentially perpendicular to a surface thereof. As shown by FIG. 8b, each of said first (BK1) and second (BK2) Berek-type retarders can have fast axis which are oriented other than parallel to one another, but for the presently described retarder system it is assumed that the fast axes are aligned, (ie. an angle PHI (φ) of zero (0.0) degrees exists between fast axes of the two Berek-type (BK1) and (BK2) plates in FIG. 8a. Said first and second Berek-type retarders each present with first and second essentially parallel sides. Said first (BK1) and second (BK2) Berek-type retarders are oriented, as viewed in side elevation, with first (LS1) and second (RS1) sides of one Berek-type retarder (BK1) being oriented other than parallel to first (LS2) and second (RS2) sides of the other Berek-type retarder (BK2). In use an incident beam of electromagnetic radiation (LB) is caused to impinge upon one of said first (BK1) Berek-type retarder on one side (LS1) thereof, partially transmit therethrough then impinge upon the second Berek-type retarder (BK2), on one side thereof (LS2), and partially transmit therethrough such that a polarized beam of electromagnetic radiation (LB') passing through both of said first (BK1) and second (BK2) Berek-type retarders emerges from the second thereof in a polarized state with a phase angle between orthogonal components therein which is different than that in the incident beam of electromagnetic radiation (LB), and in a direction which is an essentially undeviated and undisplaced from the incident beam of electromagnetic radiation. This is the case even when said retarder system (8) is caused to rotate. The result of said described retarder system (8) application being that retardation is entered between orthogonal components of said input electromagnetic beam of radiation. For insight it is mentioned that, in general, a Berek-type retarder is a uniaxial anisotropic plate with its optical axis essentially perpendicular to a surface thereof. The retardence introduced to an electromagnetic beam caused to transmit therethrough is determined by a tipping of said plate. The retardation system (8) having two such Berek-type retarders present, is, it is noted, insensitive to small angular deviations in an input electromagnetic beam as each plate contributes approximately hal of achieved retardence. This insensitivity results because if the input electromagnetic beam is slightly changed, one of said plates will contribute slightly more (less), but the second slightly less (more) retardence because of offsetting effective plate "tilts" with respect to electromagnetic beams input thereto. Also, said retarder system (8) is very nearly ideal in that the PSI component of the retarder system (8) is very near a constant forty-five (45) degrees. One problem however, is that Berek-type retarder plates exhibit a (1/wavelength) retardence characteristic which, without more, makes use over a wide spectral range difficult.

A variation of the just described retarder system (8) applies to the seventh present invention retarder system (9) as well, with the difference being that a FIG. 8b offset angle PHI ($\phi$) other than zero (0.0) is present between fast axes of the two Berek-type plates. The description of the system remains otherwise unchanged. The benefit derived, however, is that a flatter than (1/wavelength) retardation characteristic can be achieved thereby. This is discussed with respect to FIGS. 10a–10e following the geometric description of a four (4) Berek-type plate retarder system (10) directly, which constitutes an eighth present invention retarder system, as demonstrated in FIG. 9a.

Figure 9A:
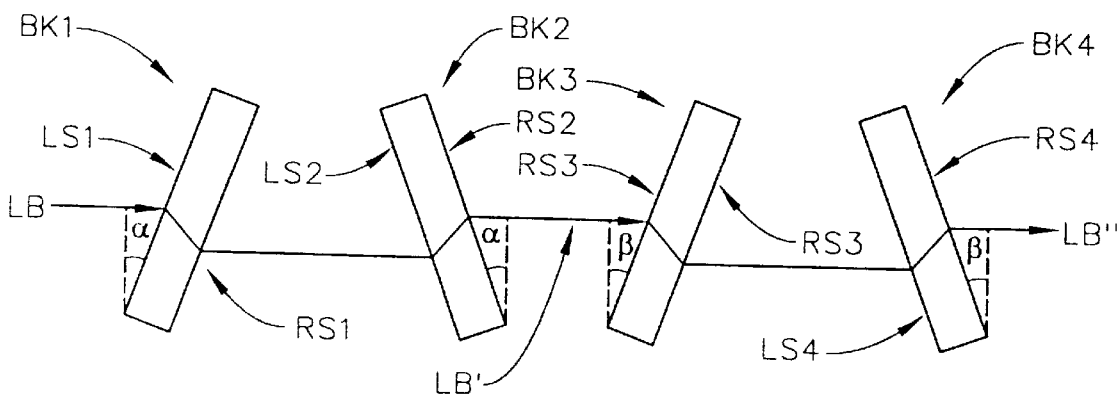
FIG. 9a shows a retarder system consisting of two dual Berek-type plate retarder systems.
Figure 9B:
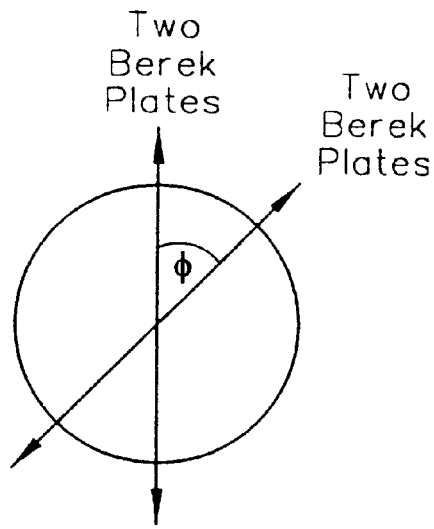

FIG. 9a serves as the pictorial reference for the eighth present invention retarder system (8) which again comprises first (BK1), second (BK2), third (BK3) and forth (BK4) Berek-type retarders which each have an optical axes essentially perpendicular to a surface thereof, each of which first (BK1) and second (BK2) Berek-type retarders has a fast axis, said fast axes in said first (BK1) and second (BK2) Berek-type retarders being oriented essentially parallel to one another. Said first (BK1) Berek-type retarder presents with first (LS1) and second (RS1) essentially parallel sides and said second (BK2) Berek-type retarders each present with first (LS2) and second (RS2) essentially parallel sides, and said first (BK1) and second (BK2) Berek-type retarders are oriented, as viewed in side elevation, with first (LS1) and second (RS1) sides of said first Berek-type retarder being oriented other than parallel to first (LS2) and second (RS2) sides of said second (BK2) Berek-type retarder. In use an incident beam of electromagnetic radiation (LB) is caused to impinge upon said first (BK1) Berek-type retarder on said first side (LS1) thereof, partially transmit therethrough then impinge upon the second (BK2) Berek-type retarder, on said first (LS2) side thereof, and partially transmit therethrough such that a polarized beam of electromagnetic radiation (LB') passing through both of said first (BK1) and second (BK2) Berek-type retarders emerges from the second thereof in a polarized state with a phase angle between orthogonal components therein which is different than that in the incident beam of electromagnetic radiation (LB), and in a direction which is an essentially undeviated and undisplaced from the incident beam of electromagnetic radiation (LB). Each of which third (BK3) and forth (BK4) Berek-type retarders also has a fast axis, and said fast axes in said third (BK3) and forth (BK4) Berek-type retarders are oriented essentially parallel to one another but other than parallel to the parallel fast axes of said first (BK1) and second (BK2) Berek-type retarders. Said third (BK3) Berek-type retarder presents with first (LS3) and second (RS3) essentially parallel sides, and said forth (BK4) Berek-type presents with first (LS4) and second (RS4) essentially parallel sides, and said first third (BK3) and forth (BK4) Berek-type retarders are oriented, as viewed in side elevation, with first (LS3) and second (RS3) sides of one of said third (BK3) Berek-type retarder being oriented other than parallel to first (LS4) and second (RS4) sides of said forth (BK4) Berek-type retarder; such that in use an incident beam of electromagnetic radiation (LB') exiting said second (BK2) Berek-type retarder is caused to impinge upon said third (BK3) Berek-type retarder on said first (LS3) side thereof, partially transmit therethrough then impinge upon said forth (BK4) Berek-type retarder on said first (LS4) side thereof, and partially transmit therethrough such that a polarized beam of electromagnetic radiation (LB") passing through said first (BK1), second (BK2), third (BK3) and forth (BK4) Berek-type retarders emerges from the forth (BK4) thereof in a polarized state with a phase angle between orthogonal components therein which is different than that in the incident beam of electromagnetic radiation (LB) caused to impinge upon the first (LS1) side of said first (BK1) Berek-type retarder, in a direction which is an essentially undeviated and undisplaced from said incident beam of electromagnetic radiation (LB). This is the case even when said retarder system (8) is caused to rotate. The result of said described retarder system (8) application being that retardation is entered between orthogonal components of said input electromagnetic beam of radiation.

Figure 10A:
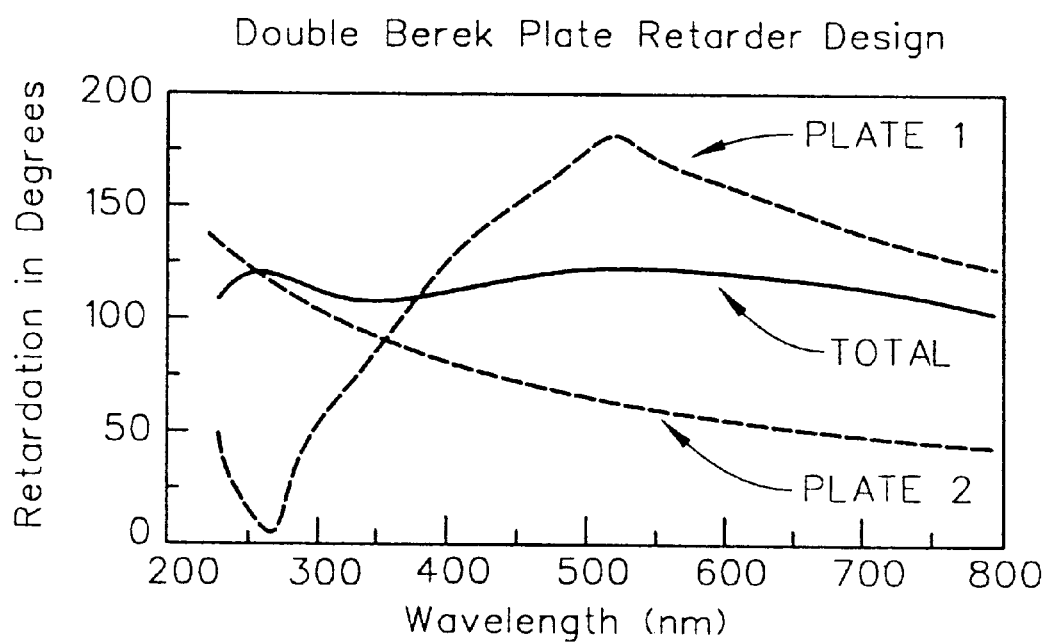
FIG. 10a shows calculated predicted individual retardation curves vs. wavelength for two separate Berek-type retarder plates in a FIG. 8a retarder system, and the combined result.
Figure 10E:
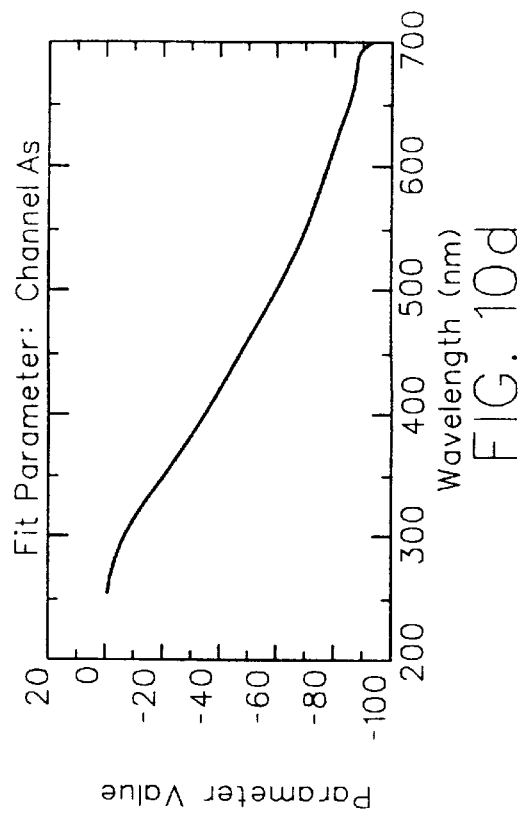
FIG. 10e shows that the measured PSI-like component of the prototype dual Berek-type retarder system of FIG. 8a are very constant.
Figure 10B:
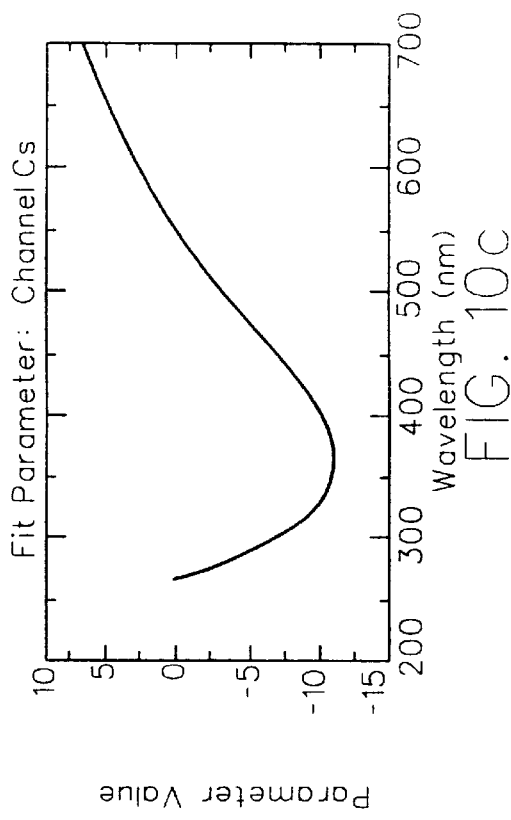
Figure 10D:
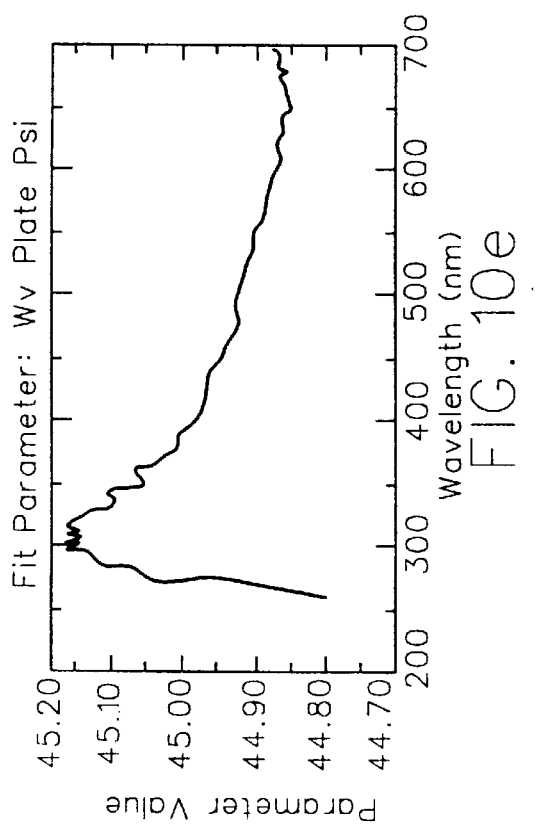
FIG. 10d shows measured relative rotor angle imposed upon a polarized beam of electromagnetic radiation caused to pass through the prototype dual Berek-type plate retarder system of FIG. 8a is not constant over a range of wavelengths.
Figure 10C:
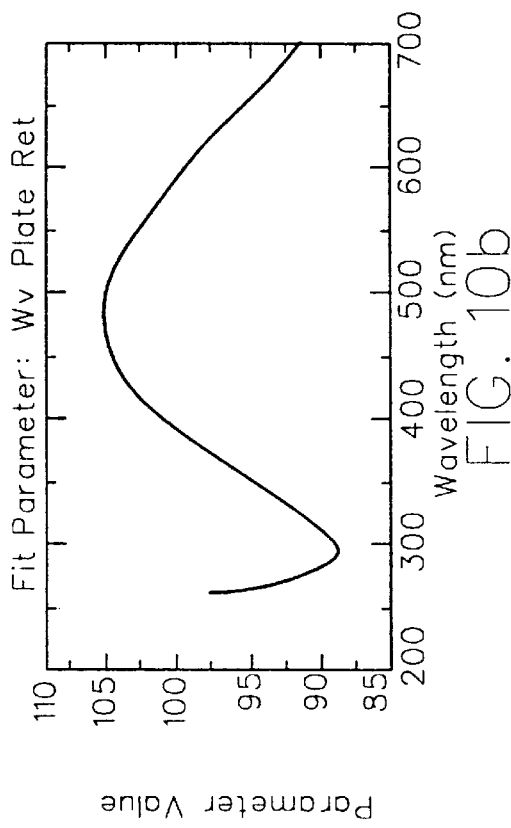
FIG. 10c shows measured fast axis orientation of the prototype dual plate Berek-type retarder system as in FIG. 8a is not constant over a range of wavelengths.

A ninth present invention retarder system (9) is also pictorially represented by FIG. 9a and is similar to that just described excepting that the Berek-type retarder plates (BK1) and (BK2) fast axes need not be parallel to one another and the Berek-type retarder plates (BK3) and (BK4) need not be parallel to one another. However, if as a group Berek-type retarder plates ((BK1) and (BK2))/((BK3) and (BK4)) are parallel, they can be, but need not be parallel the fast axes of Berek-type retarder plates ((BK3) and (BK4))/((BK1) and (BK2)). This embodiment includes the case where all the fast axes of all Berek-type retarders (BK1), (BK2), (BK3) and (BK4) are all different. Turning now to FIGS. 10a–10e there are shown the results which document the benefits of use of more than one Berek-type retarder plate with an angle present between fast axes thereof. FIG. 10a shows a calculated predicted retardence of a FIG. 8a double plate Berek-type retarder system (8). The two dashed curves show individually the retardence of each Berek-type plate individually. It is noted that the first (BK1) Berek-type plate provides quarter-wave retardence at three-hundred-fifty (350) nm and the second (BK2) Berek-type plate provides quarter wave retardence at one-thousand-fifty (1050) nm, and both exhibit (1/wavelength) dispersion in retardance as a function of wavelength. The solid curve shows the resulting combined retardence for the dual Berek-type plate retarder system (8) where the FIG. 8b PHI ($\phi$) angle is set to fifty-four (54) degrees. Note that said solid curve lies between one-hundred (100) and one-hundred-twenty (120) degrees over the spectral range of two-hundred-thirty (230) to eight-hundred (800) nm. A prototype dual plate Berek-type retarder system (8), the operational characteristics of which should be predicted by the just presented calculated results, was formed utilizing two Magnesium Fluoride (MgF$_2$) Berek-type plates which were each approximately 2 mm think. The fast axes of said two Berek-type plates were set fifty-four (54) degrees apart and retardence of the system was measured over a wavelength range. The results are shown in FIG. 10b. While the results are not as good as predicted, they are very good and actually are satisfactory for use in many ellipsometer settings. Another measurement was performed to determine the orientation of the relative fast axis of the combined dual Berek-type plate retarder system (8). FIG. 10c shows that said orientation is not constant over a range of wavelengths. FIG. 10d shows relative rotor angle imposed upon a polarized beam of electromagnetic radiation caused to transmit through the prototype dual Berek-type plate retarder system (8). Ideally a retarder system should impose no rotation, and most single wavelength retarder plates meet this criteria. It is noted that while the orientation of the relative fast axis and the relative rotor angle vs. wavelength characteristics demonstrated by the prototype dual Berek-type plate retarder system (8) are not ideal, mathematical modeling in ellipsometry practice can easily account therefore. In view thereof, the conclusion then is that the prototype dual Berek-type plate retarder system (8) investigated is suitable for application in ellipsometer/polarimeter systems. In addition, the PSI-like component of the prototype dual Berek-type retarder system (8) was also investigated, and the results are shown in FIG. 10e. It is noted that said results are constant over the shown wavelength range, to within two-tenths (0.2) degrees of the ideal forty-five (45) degrees.

In a general sense the present invention can be considered to comprise, in a spectroscopic ellipsometer/polarimeter, at least one selection from the group consisting of: (a polarizer system and a compensator system), said at least one of said polarizer and/or compensator system(s) being of a design such that in use an incident beam of electromagnetic radiation is caused to impinge upon a side of said at least one said polarizer or compensator system along a propagation direction which is other than perpendicular to a surface of said side thereof. At said side, said incident beam of electromagentic radiation at least partially reflects from said surface of said side or at least partially transmit through said surface of said side. This is followed by at least one additional at least partial reflection from, or at least partial transmission through a surface of a second side of said at least one selection from the group consisting of: (a polarizer system and a compensator system), with the result being an emerging beam of electromagnetic radiation in a state of polarization which is altered as compared to that of said incident beam of electromagentic radiation, but which emerging beam of electromagnetic radiation proceeds in a propagation direction essentially undeviated and undisplaced from the propagation direction of said incident beam of electromagnetic radiation.

As alluded to, the present invention can comprise the present invention dual wire grid polarizer in functional combination with any of the recited retarder systems, particularly in the context of a polarimeter/ellipsometer system. Said combinations are all unique in view of known prior art, and all said combinations can provide excellent electromagnetic beam polarization and retardation control, without introducing significant deviation or displacement into said beam of electromagnetic which is radiation caused to transmit therethrough, even where said retarder is caused to continuously rotate. This is true over a large range of wavelenths, including in the infrared. Those skilled in the art will appreciate the achievement demonstrated by the results disclosed.

Having hereby disclosed the subject matter of the present invention, it should be apparent that many modifications, substitutions, and variations of the present invention are possible in light thereof. It is to be understood that the present invention can be practiced other than as specifically described and should be limited in scope and breadth only by the appended claims.

We claim:

1. In a spectroscopic ellipsometer/polarimeter system, a retarder system comprising a first triangular shaped element, which as viewed in side elevation presents with first and second sides which project to the left and right and downward from an upper point, which first triangular shaped element first and second sides have reflective outer surfaces; said retarder system further comprising a second triangular shaped element which as viewed in side elevation presents with first and second sides which project to the left and right and downward from an upper point, said second triangular shaped element being made of material which provides reflective interfaces on first and second sides inside thereof; said second triangular shaped element being oriented with respect to the first triangular shaped element such that the upper point of said second triangular shaped element is oriented essentially vertically directly above the upper point of said first triangular shaped element; such that in use an input electromagnetic beam of radiation caused to approach one of said first and second sides of said first triangular shaped element along an essentially horizontally oriented locus, and regardless of polarization state, is caused to externally reflect from an outer surface thereof and travel along a locus which is essentially upwardly vertically oriented, then enter said second triangular shaped element and essentially totally internally reflect from one of said first and second sides thereof, then proceed along an essentially horizontal locus and essentially totally internally reflect from the other of said first and second sides and proceed along an essentially downward vertically oriented locus, then externally reflect from the other of said first and second sides of said first triangular shaped elements and proceed along an essentially horizontally oriented locus which is undeviated and undisplaced from the essentially horizontally oriented locus of said input beam of essentially horizontally oriented electromagnetic radiation even when said retarder system is caused to rotate about the locus of said beam of essentially horizontally oriented electromagnetic radiation; with a result being that retardation is entered between orthogonal components of said input electromagnetic beam of radiation.

2. In a spectroscopic ellipsometer/polarimeter system as in claim 1, a polarizer system comprising first and second non-Brewster angle polarizers which each have fast axes of polarization and which fast axes of polarization are oriented with their directions of polarization essentially parallel to one another, said first and second non-Brewster angle polarizers each presenting with first and second essentially parallel sides, and said first and second non-Brewster angle polarizers being oriented, as viewed in side elevation, with first and second sides of one non-Brewster angle polarizer oriented other than parallel to first and second sides of the other non-Brewster angle polarizer; such that in use an incident beam of electromagnetic radiation is caused to impinge upon one of said first and second non-Brewster angle polarizers on one side thereof, partially reflect therefrom and partially transmit therethrough, then impinge upon the other non-Brewster angle polarizer on one side thereof, partially reflect therefrom and partially transmit therethrough, such that a beam of electromagnetic radiation passing through both of said first and second non-Brewster angle polarizers emerges from the second thereof in a polarized state in a propagation direction which is essentially undeviated and undisplaced from the incident beam of electromagnetic radiation, with the resulting reflected electromagnetic beam portions being directed away from said emerging polarized beam of electromagnetic radiation.

3. A method of practicing ellipsometry/polarimetry comprising the steps of:

a. providing a spectroscopic ellipsometer/polarimeter system sequentially comprising:

a source of electromagnetic radiation;

at least one selection from the group consisting of:

a non-Brewster angle dual wire grid polarizer system and a compensator system;

said at least one selection from the group consisting of:

a wire non-Brewster angle dual grid polarizer system and a compensator system being of a design such that in use an incident beam of electromagnetic radiation is caused to impinge upon a side thereof along a propagation direction which is other than perpendicular to a surface of said side thereof and undergo at least one interaction therewith selected from the group consisting of:

at least partially reflect from said surface of said side; and at least partially transmit through said surface of said side;

such that at least a portion of said beam of electromagnetic radiation emerges from said at least one selection from the group consisting of:

a non-Brewster angle dual wire grid polarizer system and a compensator system;

after undergoing at least one additional interaction therewith selected from the group consisting of:

at least partial reflection from, and at least partial transmission through a surface of a second side of said at least one selection from the group consisting of:

a non-Brewster angle dual wire grid polarizer system and a compensator system;

said emerging beam of electromagnetic radiation being in a state of polarization which is altered as compared to that of said incident beam of electromagnetic radiation, but which emerging beam of electromagnetic radiation proceeds in a propagation direction essentially undeviated and undisplaced from the propagation direction of said incident beam of electromagnetic radiation;

an analyzer system; and a detector system;

b. placing a sample system into said spectroscopic ellipsometer/polarimeter system;

c. causing said source of electromagnetic radiation to provide a beam of electromagnetic radiation to said sample; and d. detecting said beam of electromagnetic radiation after interaction thereof with said sample system.

4. A method of practicing ellipsometry/polarimetry comprising the steps of:

a. providing a spectroscopic ellipsometer/polarimeter system sequentially comprising:

a source of spectroscopic electromagnetic radiation;

at least one retarder system comprising a first triangular shaped element, which as viewed in side elevation presents with first and second sides which project to the left and right and downward from an upper point, which first triangular shaped element first and second sides have reflective outer surfaces; said retarder system further comprising a second triangular shaped element which as viewed in side elevation presents with first and second sides which project to the left and right and downward from an upper point, said second triangular shaped element being made of material which provides reflective interfaces on first and second sides inside thereof; said second triangular shaped element being oriented with respect to the first triangular shaped element such that the upper point of said second triangular shaped element is oriented essentially vertically directly above the upper point of said first triangular shaped element; such that in use an input electromagnetic beam of radiation caused to approach one of said first and second sides of said first triangular shaped element along an essentially horizontally oriented locus, and regardless of polarization state, is caused to externally reflect from an outer surface thereof and travel along a locus which is essentially upwardly vertically oriented, then enter said second triangular shaped element and essentially totally internally reflect from one of said first and second sides thereof, then proceed along an essentially horizontal locus and essentially totally internally reflect from the other of said first and second sides and proceed along an essentially downward vertically oriented locus, then externally reflect from the other of said first and second sides of said first triangular shaped elements and proceed along an essentially horizontally oriented locus which is undeviated and undisplaced from the essentially horizontally oriented locus of said input beam of essentially horizontally oriented electromagnetic radiation even when said retarder system is caused to rotate about the locus of said beam of essentially horizontally oriented electromagnetic radiation; with a result being that retardation is entered between orthogonal components of said input electromagnetic beam of radiation;

an analyzer system; and a detector system;

b. placing a sample system into said spectroscopic ellipsometer/polarimeter system;

c. causing said source of electromagnetic radiation to provide a beam of electromagnetic radiation to said sample system, and also pass through said at least one retarder system; and d. detecting said beam of electromagnetic radiation after interaction thereof with said sample system.

5. A method of practicing ellipsometry/polarimetry as in claim 4 which further comprises the step of:

causing said compensator/retarder system to rotate about said locus of said beam of electromagnetic radiation;

while detecting said beam of electromagnetic radiation in step d.

6. A compensator/retarder system comprising:

a first triangular shaped element having first and second sides which project at an angle with respect to one another from a common point, said first and second sides of said first triangular shaped element being made of a material which provides that said first and second sides have externally reflective surfaces;

said compensator/retarder system further comprising a second triangular shaped element which presents with first and second sides which project at an angle with respect to one another from a common point, said second triangular shaped element being made of material which provides reflective interfaces on first and second sides inside thereof;

said second triangular shaped element being oriented with respect to said first triangular shaped element such that in use an input electromagnetic beam of radiation caused to approach one of said first and second sides of said first triangular shaped element, and regardless of polarization state, is caused to externally reflect therefrom and enter said second triangular shaped element element and essentially totally internally reflect from one of said first and second sides thereof, then essentially totally internally reflect from the other of said first and second sides and then proceed to and reflect from the other of said first and second sides of said first triangular shape element and proceed along a propagation direction locus which is essentially undeviated and undisplaced from that of said input electromagnetic beam of radiation, even when said compensator/retarder is caused to rotate about the locus of said beam of electromagnetic radiation; with a result being that retardation is entered between orthogonal components of said input electromagnetic beam of radiation.

7. In a spectroscopic ellipsometer/polarimeter system, a compensator/retarder system comprising:

a first triangular shaped element having first and second sides which project at an angle with respect to one another from a common point, said first and second sides of said first triangular shaped element being made of a material which provides that said first and second sides have externally reflective surfaces;

said compensator/retarder system further comprising:

a second triangular shaped element which presents with first and second sides which project at an angle with respect to one another from a common point, said second triangular shaped element being made of material which provides reflective interfaces on first and second sides inside thereof;

said second triangular shaped element being oriented with respect to said first triangular shaped element such that in use an input electromagnetic beam of radiation caused to approach one of said first and second sides of said first triangular shaped element, is caused to externally reflect therefrom and enter said second triangular shaped element element and essentially totally internally reflect from one of said first and second sides thereof, then essentially totally internally reflect from the other of said first and second sides and then proceed to and reflect from the other of said first and second sides of said first triangular shape element and proceed along a propagation direction locus which is essentially undeviated and undisplaced from that of said input electromagnetic beam of radiation, even when said compensator/retarder is caused to rotate about the locus of said beam of electromagnetic radiation; with a result being that retardation is entered between orthogonal components of said input electromagnetic beam of radiation.

8. A method of practicing ellipsometry/polarimetry comprising the steps of:

a. providing an ellipsometer/polarimeter system sequentially comprising:

a source of electromagnetic radiation;

at least one retarder system which comprises:

a first triangular shaped element having first and second sides which project at an angle with respect to one another from a common point, said first and second sides of said first triangular shaped element being made of a material which provides that said first and second sides have externally reflective surfaces;

said compensator/retarder system further comprising:

a second triangular shaped element which presents with first and second sides which project at an angle with respect to one another from a common point, said second triangular shaped element being made of material which provides reflective interfaces on first and second sides inside thereof;

said second triangular shaped element being oriented with respect to said first triangular shaped element such that in use an input electromagnetic beam of radiation caused to approach one of said first and second sides of said first triangular shaped element, and regardless of polarization state, is caused to externally reflect therefrom and enter said second triangular shaped element element and essentially totally internally reflect from one of said first and second sides thereof, then essentially totally internally reflect from the other of said first and second sides and then proceed to and reflect from the other of said first and second sides of said first triangular shape element and proceed along a propagation direction locus which is essentially undeviated and undisplaced from that of said input electromagnetic beam of radiation, even when said compensator/retarder is caused to rotate about the locus of said beam of electromagnetic radiation; with a result being that retardation is entered between orthogonal components of said input electromagnetic beam of radiation;

an analyzer system; and a detector system;

b. placing a sample system into said ellipsometer/polarimeter system;

c. causing said source of electromagnetic radiation to provide a beam of electromagnetic radiation to said sample system and also pass through said at least one retarder system; and d. detecting said beam of electromagnetic radiation after interaction thereof with said sample system.

9. A method of practicing ellipsometry/polarimetry as in claim 8 which further comprises the step of:

causing said compensator/retarder system to rotate about said locus of said beam of electromagnetic radiation;

while detecting said beam of electromagnetic radiation in step d.

* * * * *